United States Patent
Fuwamoto et al.

(10) Patent No.: US 7,945,313 B2
(45) Date of Patent: May 17, 2011

(54) METHOD AND DEVICE FOR MONITORING HEART RHYTHM IN A VEHICLE

(75) Inventors: Yoshitaka Fuwamoto, Toyota (JP); Takao Katoh, Tokyo (JP); Tsuyoshi Nakagawa, Aichi-ken (JP); Taiji Kawachi, Kariya (JP)

(73) Assignees: Toyota Jidosha Kabushiki Kaisha, Toyota-shi, Aichi-ken (JP); Nippon Medical School Foundation, Tokyo (JP); Denso Corporation, Aichi-Pref (JP)

( * ) Notice: Subject to any disclaimer, the term of this patent is extended or adjusted under 35 U.S.C. 154(b) by 1015 days.

(21) Appl. No.: 11/798,070

(22) Filed: May 10, 2007

(65) Prior Publication Data
US 2007/0265540 A1    Nov. 15, 2007

(30) Foreign Application Priority Data
May 10, 2006   (JP) .................................. 2006-131855

(51) Int. Cl.
*A61B 5/0408* (2006.01)
(52) U.S. Cl. ...................................................... 600/509
(58) Field of Classification Search .................. 600/508, 600/509; 180/271; 340/425.5
See application file for complete search history.

(56) References Cited

U.S. PATENT DOCUMENTS
2003/0073886 A1 * 4/2003 Yanagidaira et al. ......... 600/300
2010/0049068 A1 * 2/2010 Fuwamoto et al. ........... 600/509

FOREIGN PATENT DOCUMENTS
JP         2004-261580      9/2004
* cited by examiner

*Primary Examiner* — Carl H. Layno
*Assistant Examiner* — Jon-Eric Morales
(74) *Attorney, Agent, or Firm* — Finnegan, Henderson, Farabow, Garrett & Dunner, LLP

(57) ABSTRACT

An heart rhythm monitoring device for a vehicle, which determines whether a driver has an arrhythmia includes a vehicle state determining portion that determines whether the vehicle is stopped; an electrode arranged on a steering wheel in a position where the driver grips the steering wheel; an electrocardiogram waveform obtaining portion that obtains a first electrocardiogram waveform from the electrode; and a signal processing and calculating portion that determines whether the heart rhythm of the driver is erratic based on the first electrocardiogram waveform. When the vehicle is in motion, the signal processing and calculating portion determines whether the heart rhythm of the driver is erratic based on the waveform component that is strong with respect to noise in the first electrocardiogram waveform.

13 Claims, 5 Drawing Sheets

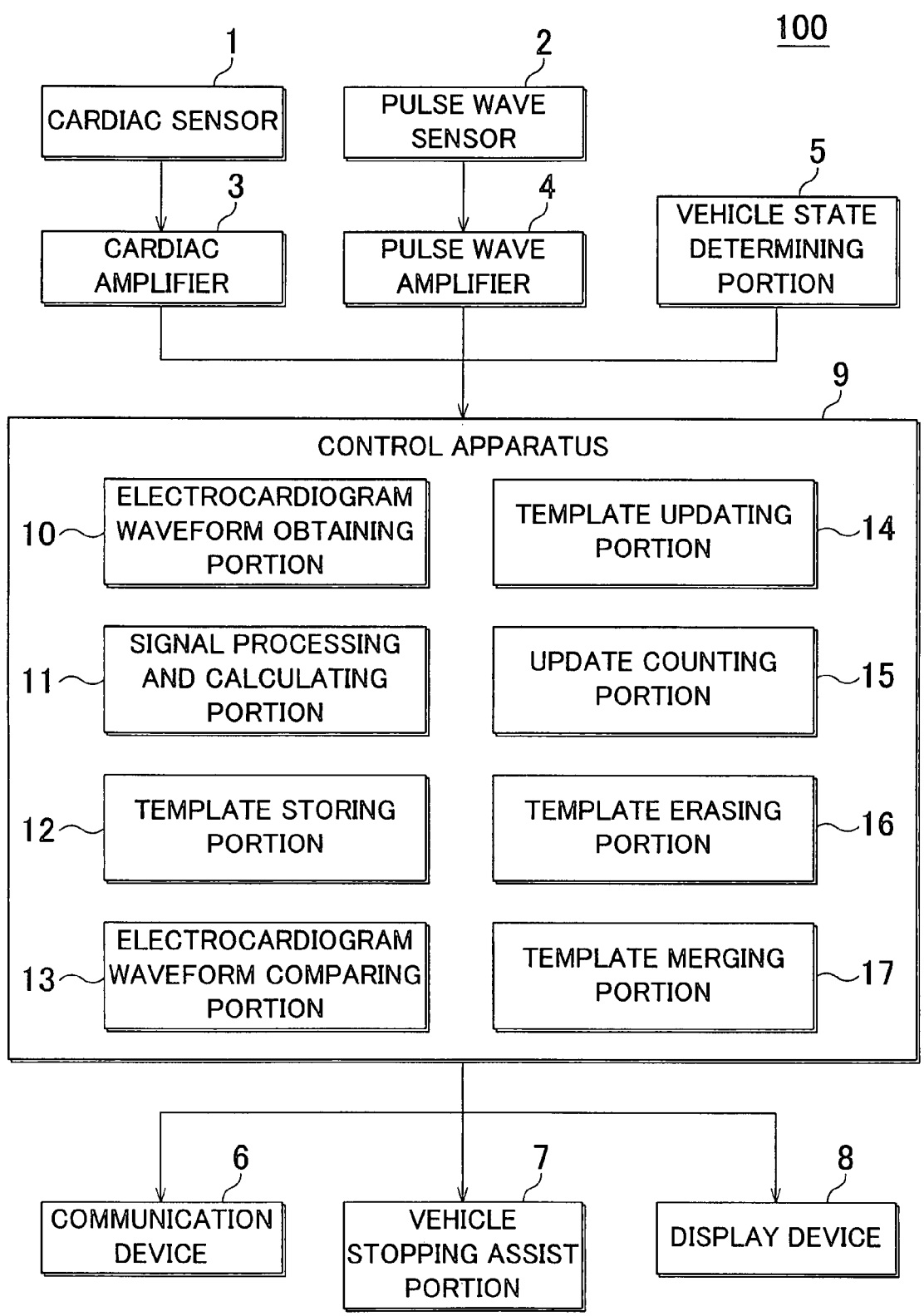

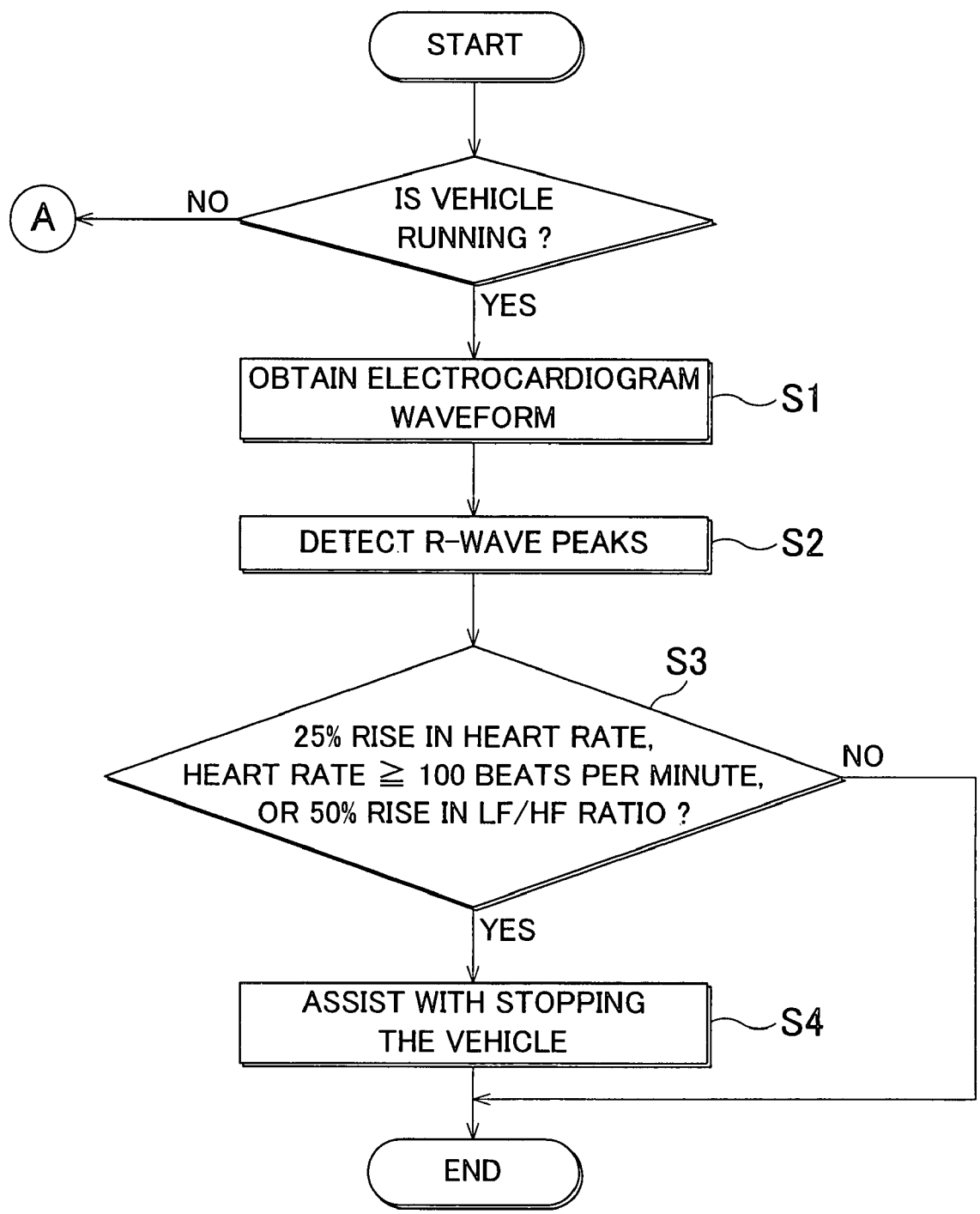

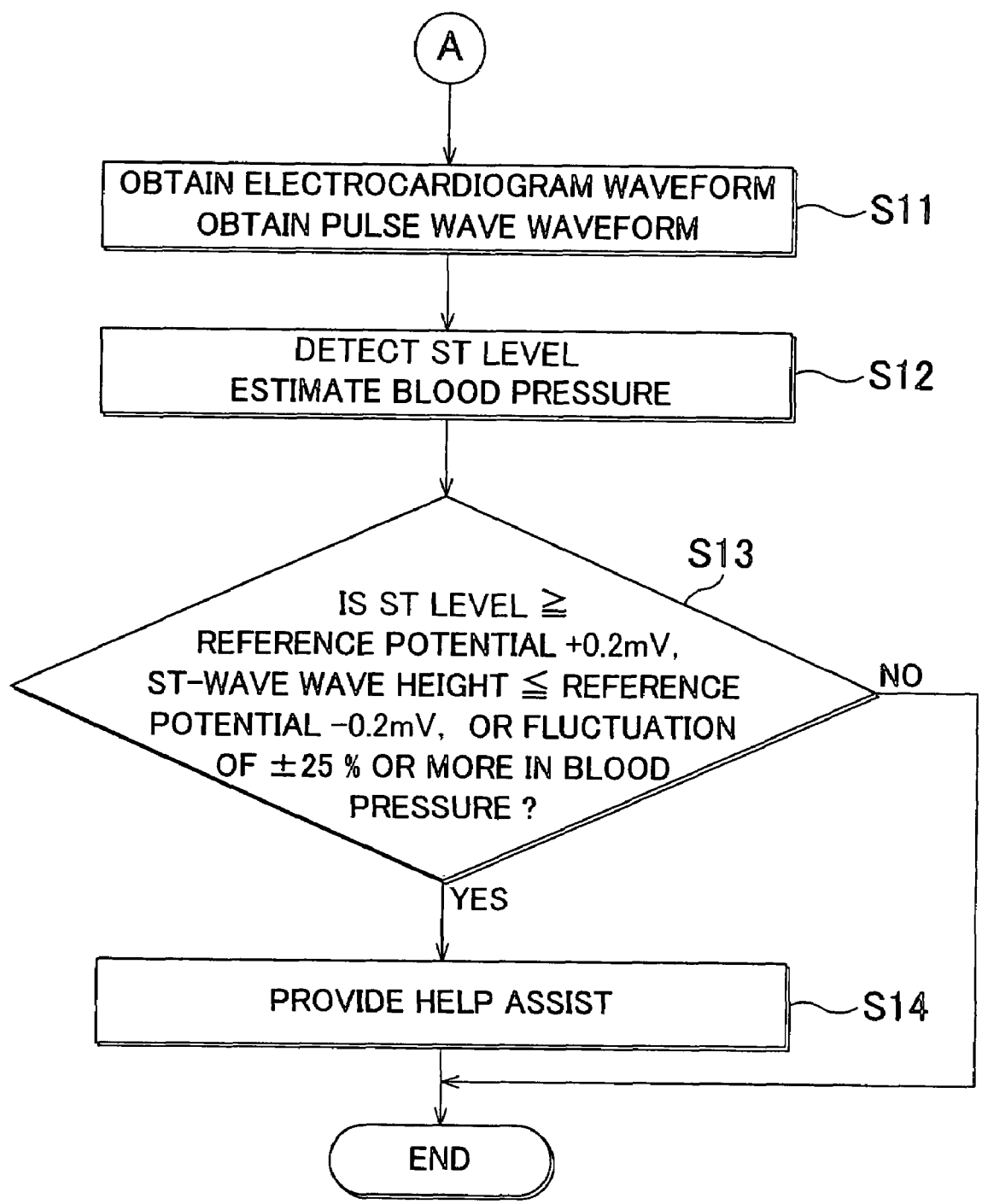

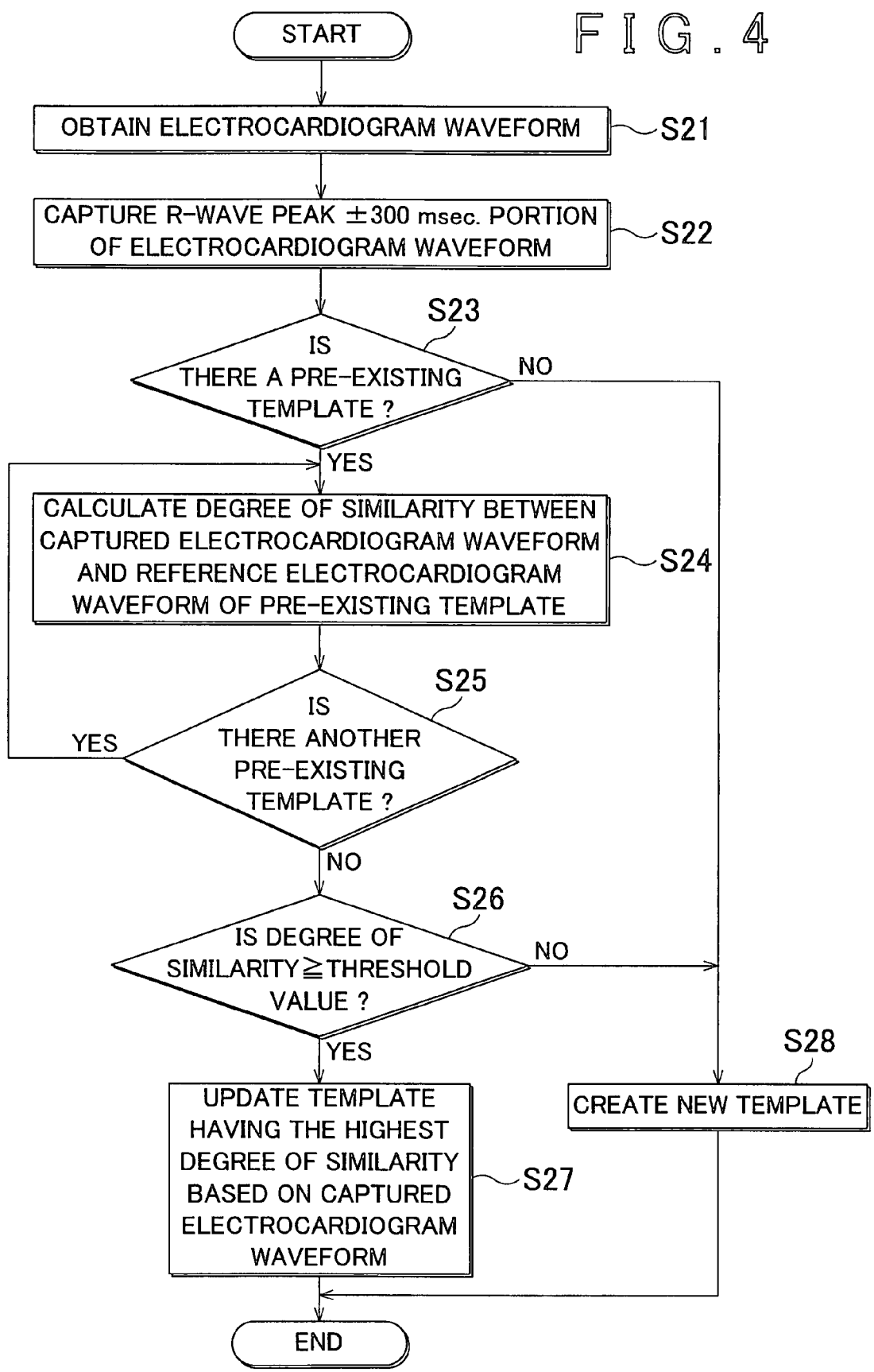

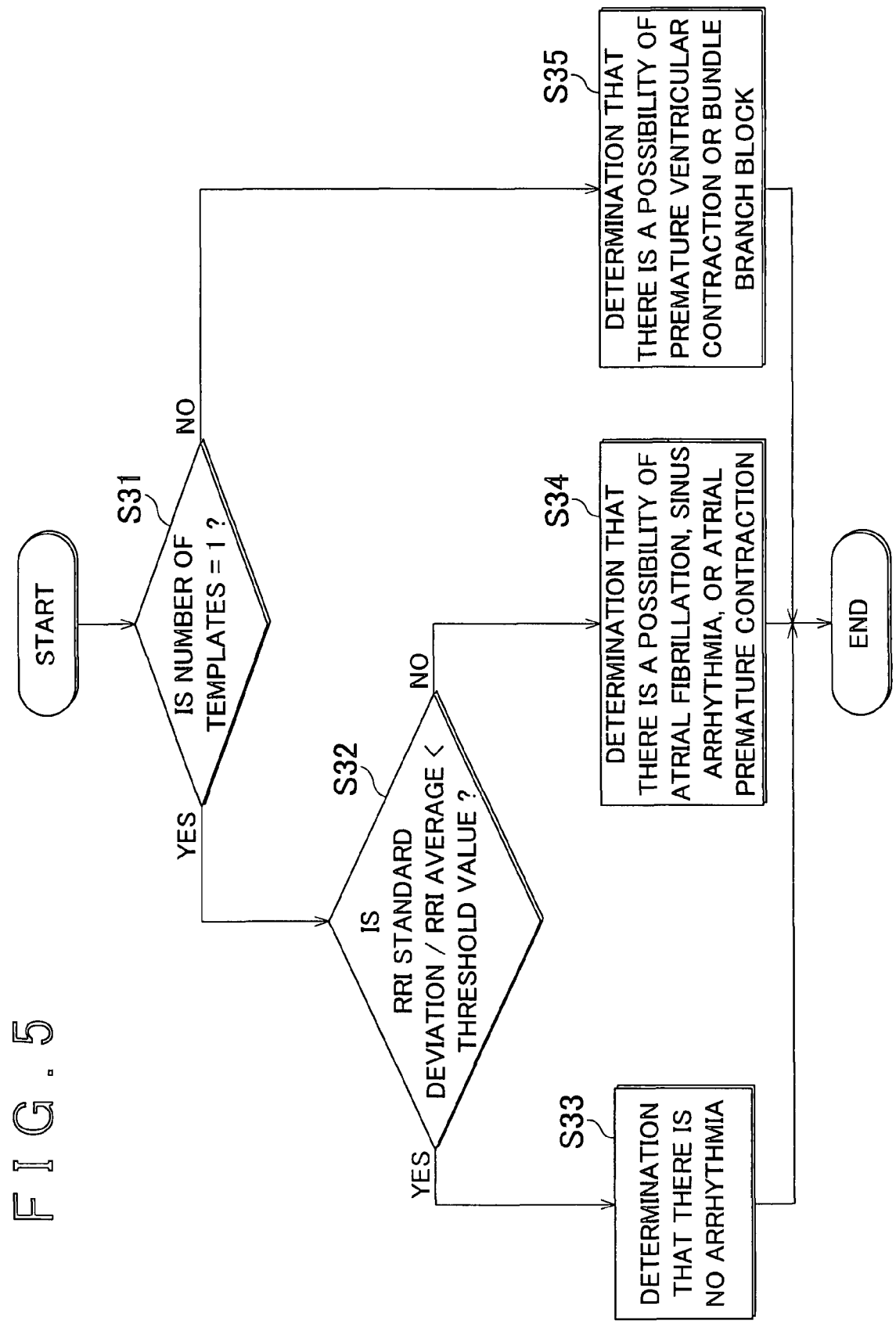

METHOD AND DEVICE FOR MONITORING HEART RHYTHM IN A VEHICLE

INCORPORATION BY REFERENCE

The disclosure of Japanese Patent Application No. 2006-131855 filed on May 10, 2006, including the specification, drawings and abstract is incorporated herein by reference in its entirety.

BACKGROUND OF THE INVENTION

1. Field of the Invention

The invention relates to a heart-rhythm monitoring device for a vehicle, and more particularly, to a device and method for monitoring heart rhythm in a vehicle that reliably determines whether a driver has an arrhythmia while driving the vehicle.

2. Description of the Related Art

Devices for monitoring the cardiac status of a driver are becoming increasingly important in aging societies to prevent traffic accidents that occur as a result of cardiovascular disorder (i.e., heart disease). This is because if an individual at risk of having life-threatening arrhythmia goes into cardiac arrest and loses consciousness while driving, for example, the vehicle driven by that individual is more likely to cause a serious accident.

One device for monitoring the cardiac status of an individual is an electrocardiogram or ECG monitor that measures cardiac electrical activities. In particular, an ambulatory Holter monitoring can record electrocardiogram for 24 hours or more. The fact that the Holter monitor can non-invasively measure cardiac status simply with electrodes attached to the body surface makes it suitable for measuring the cardiac status of a driver.

However, in order for a cardiac abnormality to be confirmed, the electrocardiogram waveforms recorded over a predetermined period of time by the Holter monitor must first be checked by a doctor or other individual with knowledge in that field. The Holter monitor is not designed to predict a cardiac abnormality and automatically take the necessary measures.

On the other hand, Japanese Patent Application Publication No. JP-A-2004-261580, for example, describes a cardiosaver device which is a self-contained implanted device that predicts an acute myocardial infarction (AMI) based on results from monitoring the ST segment of the electrocardiogram waveform and issues an alarm. When a predetermined electrocardiogram waveform is detected, the cardiosaver device transmits a signal that indicates the cardiac status of the individual wearing the device to the wearer and an external medical institution or the like.

However, the cardiosaver device described in Japanese Patent Application Publication No. JP-A-2004-261580 is based on monitoring the ST segment of the electrocardiogram waveform, and is thus cannot be applied to a case where it is difficult to accurately measure the ST segment due to myoelectric noise, or the like, that is produced while driving.

SUMMARY OF THE INVENTION

This invention thus provides a heart rhythm monitoring device and method for a vehicle, which reliably determines whether a driver has an arrhythmia even while driving the vehicle.

A first aspect of the invention thus relates to a heart-rhythm monitoring device for a vehicle, which determines whether a driver has an arrhythmia based on an electrocardiogram waveform having a waveform component that is strong with respect to noise and a waveform component that is not strong with respect to noise. The heart-rhythm monitoring device for a vehicle includes a vehicle-state determining portion that determines whether the vehicle is stopped; an electrode that is arranged on a steering wheel in a position where the driver grips the steering wheel; an electrocardiogram waveform obtaining portion that obtains a first electrocardiogram waveform from the electrode; and a signal processing and calculating portion that determines whether the heart rhythm of the driver is erratic based on the first electrocardiogram waveform. When the vehicle-state determining portion determines that the vehicle is not stopped, the signal processing and calculating portion determines whether the heart rhythm of the driver is erratic based on the waveform component that is strong with respect to noise in the first electrocardiogram waveform.

Also, according to a second aspect of the invention, in the heart-rhythm monitoring device for a vehicle according to the first aspect, the waveform component that is strong with respect to noise may be an R-wave component of the first electrocardiogram waveform.

Further, according to a third aspect of the invention, the heart-rhythm monitoring device for a vehicle according to the first aspect may also include a vehicle stopping assist portion that assists the driver in stopping the vehicle when the vehicle-state determining portion determines that the vehicle is not stopped and the signal processing and calculating portion determines that the heart rhythm of the driver is erratic.

Also, according to a fourth aspect of the invention, in the heart-rhythm monitoring device for a vehicle according to the first aspect, when the vehicle state determining portion determines that the vehicle is stopped, a second electrocardiogram waveform is obtained and the signal processing and calculating portion may determine whether the heart rhythm of the driver is erratic based on a waveform component other than the waveform component that is strong with respect to noise in the second waveform electrocardiogram.

Also, according to a fifth aspect of the invention, the heart-rhythm monitoring device for a vehicle according to the first aspect may also include a pulse wave sensor that obtains a pulse wave waveform from the electrode. When the vehicle state determining portion determines that the vehicle is stopped, a second electrocardiogram waveform may be obtained and the signal processing and calculating portion may determine whether the heart rhythm of the driver is erratic based on the pulse wave waveform and a waveform component other than the waveform component that is strong with respect to noise in the second electrocardiogram waveform.

Also, according to a sixth aspect of the invention, the heart-rhythm monitoring device for a vehicle according to the first aspect may also include a template storing portion that stores at least one template having a reference electrocardiogram waveform; an electrocardiogram waveform comparing portion that determines whether the first electrocardiogram waveform resembles the reference electrocardiogram waveform of each of the at least one template stored in the template storing portion; and a template updating portion. When the electrocardiogram waveform comparing portion determines that the first electrocardiogram waveform resembles the reference electrocardiogram waveform of a first template of the at least one template stored in the template storing portion, the template updating portion may update the reference electrocardiogram waveform of the first template based on the first electrocardiogram waveform, and when the electrocardiogram waveform comparing portion determines that the first electrocardiogram waveform does not resemble the reference electrocardiogram waveform of each of the at least one template stored in the template storing portion, the template updating portion may create another template and may use the electrocardiogram waveform as the reference electrocardiogram waveform of the another template.

Also, according to a seventh aspect of the invention, in the heart-rhythm monitoring device for a vehicle according to the sixth aspect, the electrocardiogram waveform comparing portion may determine whether the first electrocardiogram waveform resembles the reference electrocardiogram waveform of the first template based on a correlation coefficient calculated between the reference electrocardiogram waveform of the first template and the first electrocardiogram waveform.

Also, according to an eighth aspect of the invention, in the heart-rhythm monitoring device for a vehicle according to the sixth aspect, the electrocardiogram waveform comparing portion may determine that the first electrocardiogram waveform resembles the reference electrocardiogram waveform of the first template when a predetermined relationship between an average height of the reference electrocardiogram waveform of the first template and the average height of the first electrocardiogram waveform is satisfied.

Also, according to a ninth aspect of the invention, in the heart-rhythm monitoring device for a vehicle according to the sixth aspect, the signal processing and calculating portion may determine whether there is atrial fibrillation based on information related to an R-wave interval when there is one template stored in the template storing portion.

Also, according to a tenth aspect of the invention, in the heart-rhythm monitoring device for a vehicle according to the sixth aspect, when there are two or more templates stored in the template storing portion, the signal processing and calculating portion may determine whether there is premature ventricular contraction based on the difference between two reference electrocardiogram waveforms from among the two or more templates.

Further, according to an eleventh aspect of the invention, the heart-rhythm monitoring device for a vehicle according to the sixth aspect may also include an update counting portion that totals the number of electrocardiogram waveforms used to update the reference electrocardiogram waveform of the first template; and a template erasing portion that erases the first template stored by the template storing portion. The template erasing portion may erase the first template i) when a predetermined period of time has passed after the reference electrocardiogram waveform of the first template was last updated, or ii) when the number of electrocardiogram waveforms totaled in the predetermined period of time by the update counting portion does not reach a predetermined number.

Also, according to a twelfth aspect of the invention, the heart-rhythm monitoring device for a vehicle according to the sixth aspect may further include a template merging portion that merges the first template and a second template of each of the at least one template stored in the template storing portion into a single template, and the template merging portion merges the first template with the second template by updating the reference electrocardiogram waveform of the second template based on the reference electrocardiogram waveform of the first template when the template merging portion has determined that the reference electrocardiogram waveform of the first template resembles the reference electrocardiogram waveform of the second template.

Also, according to a thirteenth aspect of the invention, in the heart-rhythm monitoring device for a vehicle according to the twelfth aspect, the template merging portion may merge the first template with the second template based on a ratio of the total number of electrocardiogram waveforms used to update the reference electrocardiogram waveform of the first template to the total number of electrocardiogram waveforms used to update the reference electrocardiogram waveform of the second template.

Also, a fourteenth aspect of the invention thus relates to a heart-rhythm monitoring method for a vehicle, which determines whether a driver has an arrhythmia based on an electrocardiogram waveform having a waveform component that is strong with respect to noise and a waveform component that is not strong with respect to noise. The heart-rhythm monitoring method for a vehicle may include determining whether the vehicle is stopped; obtaining an electrocardiogram waveform from an electrode that is arranged on a steering wheel in a position where the driver grips the steering wheel; and determining whether the heart rhythm of the driver is erratic based on the obtained electrocardiogram waveform. When it is determined that the vehicle is not stopped, it is determined whether the heart rhythm of the driver is erratic based on the waveform component that is strong with respect to noise in the obtained electrocardiogram waveform.

Accordingly, the foregoing aspects of the invention make it possible to provide an heart-rhythm monitoring device and a method for a vehicle which reliably determines whether a driver has an arrhythmia, even while the driver is driving vehicle.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein:

FIG. 1 is a functional block diagram of an heart rhythm monitoring device for a vehicle according to an example embodiment of the invention;

FIG. 2 is a flowchart illustrating a routine for determining whether a driver has an arrhythmia while the vehicle is running;

FIG. 3 is a flowchart illustrating a routine for determining whether the driver has an arrhythmia while the vehicle is stopped;

FIG. 4 is a flowchart illustrating a routine for updating a template of an electrocardiogram waveform; and FIG. 5 is a flowchart illustrating a routine for determining whether a driver has an arrhythmia based on the template information.

DETAILED DESCRIPTION OF THE PREFERRED EMBODIMENTS

In the following description and the accompanying drawings, the present invention will be described in more detail in terms of example embodiments.

FIG. 1 is a functional block diagram of an heart rhythm monitoring device and method for a vehicle according to an example embodiment of the invention. The heart rhythm monitoring device for a vehicle (hereinafter simply referred to as "heart rhythm monitoring device") 100 includes a cardiac sensor 1, a pulse wave sensor 2, a cardiac amplifier 3, a pulse wave amplifier 4, a vehicle state determining portion 5, a communication device 6, a vehicle stopping assist portion 7, a display device 8, and a control apparatus 9.

The cardiac sensor 1 is an electrocardiogram-waveform obtaining portion for obtaining an electrocardiogram waveform. Electrodes, not shown, for measuring cardiac electrical activities are arranged on the surface of the steering wheel, also not shown, of the vehicle. The main body of the cardiac sensor 1 is embedded in the steering wheel. The reason for arranging the electrodes on the surface of the steering wheel is so that both the left and right hands of the driver will reliably contact the electrodes. Also, the cardiac sensor 1 transmits a signal related to the obtained electrocardiogram waveform to the cardiac amplifier 3. Incidentally, the main body of the cardiac sensor 1 may alternatively be arranged in the steering column or the dashboard.

When the driver is at ease such as when the vehicle is stopped or traveling straight at a constant speed, movement of the driver is relatively small and the contact pressure between the hands of the driver and the electrodes on the surface of the steering wheel also tends to be constant so the electrocardiogram waveform obtained by the cardiac sensor 1 tends to be relatively stable. However, the electrocardiogram waveform obtained by the cardiac sensor 1 is easily affected by myoelectric noise from movement of the driver. Therefore, at times such as when the vehicle is accelerating, decelerating, or turning, the movement of the driver is also relatively large and the contact pressure between the hands of the driver and the electrodes on the surface of the steering wheel tends to vary, which tends to disturb the electrocardiogram waveform. Also, if the driver takes one hand off of the steering wheel when he or she is steering, the cardiac sensor 1 is unable to obtain an electrocardiogram waveform during that time.

The pulse wave sensor 2 calculates the blood pressure and pulse rate from the amount of blood flowing through the finger using a photoelectric element. Similar to the cardiac sensor 1, a measuring terminal portion, not shown, is arranged on the surface of the steering wheel so that the flat portions of the fingers of the driver will reliably contact it. The main body of the pulse wave sensor 2 is embedded in the steering wheel. Also, the pulse wave sensor 2 may also attach in a wrap-around fashion to the wrists of the driver and the measure the pulse and blood pressure using a piezoelectric element. Further, the pulse wave sensor 2 transmits a signal related to the obtained pulse and blood pressure to the pulse wave amplifier 4.

The cardiac amplifier 3 and the pulse wave amplifier 4 are devices that amplify the signals received from the cardiac sensor 1 and the pulse wave sensor 2, respectively. Also, the cardiac amplifier 3 and the pulse wave amplifier 4 transmit the amplified signals to the control apparatus 9.

The vehicle-state determining portion 5 determines the running state of the vehicle. This vehicle-state determining portion 5 receives signals from a various sensors such as a vehicle speed sensor, a steering angle sensor, a throttle opening amount sensor, and a brake sensor, none of which are shown, and makes various determinations such as whether the vehicle is stopped, accelerating or decelerating, or negotiating a curve or a turn or the like. Also, the vehicle-state determining portion 5 transmits the determination results to the control apparatus 9.

The communication device 6 is a device for communicating with the outside. Upon receiving a command from the control apparatus 9, the communication device 6 alerts a pre-registered contact, such as a medical institution or an ambulance, and transmits information regarding the location of the vehicle.

The vehicle stopping assist portion 7 is a device that assists the driver with operating the vehicle to safely bring the vehicle to a stop. Upon receiving a command from the control apparatus 9, the vehicle stopping assist portion 7 automatically operates the brakes to gradually decelerate the vehicle and bring it to a stop. When automatically operating the brakes, the hazard lights may also be made to flash to warn surrounding vehicles.

The display device 8 is an onboard display device such as a LCD (Liquid Crystal Display) or organic EL (Electro Luminescence) display. Upon receiving a command from the control apparatus 9, the display device 8 operates either alone or in cooperation with the vehicle stopping assist portion 7 and displays a warning message on a screen to stop the vehicle, issues an auditory message from a speaker that is provided, or flashes a warning lamp such as an LED (Light Emitting Diode).

The control apparatus 9 includes an electrocardiogram waveform obtaining portion 10, a signal processing and calculating portion 11, a template storing portion 12, an electrocardiogram waveform comparing portion 13, a template updating portion 14, an update counting portion 15, a template erasing portion 16, and a template merging portion 17. The control apparatus 9 receives signals from the cardiac amplifier 3, the pulse wave amplifier 4, and the vehicle-state determining portion 5 and determines the cardiac status of the driver. Then based on the determination results, the control apparatus 9 controls the communication portion 6, the vehicle stopping assist portion 7, and the display device 8.

The electrocardiogram waveform obtaining portion 10 obtains the electrocardiogram waveform that was obtained by the cardiac sensor 1 and amplified by the cardiac amplifier 3.

The signal processing and calculating portion 11 determines whether the heart rhythm of the driver is erratic based on the electrocardiogram waveform obtained by the electrocardiogram waveform obtaining portion 10, as well as the pulse wave waveform. Incidentally, the electrocardiogram waveform on which the determination by the signal processing and calculating portion 11 is based includes a reference electrocardiogram waveform of a template updated by the template updating portion 14 and/or a reference electrocardiogram waveform of a template created by the template merging portion 17.

Also, the signal processing and calculating portion 11 changes the waveform portion of the electrocardiogram waveform used to determine the cardiac status of the driver according to the determination results from the vehicle state determining portion 5. For example, when the vehicle state determining portion 5 determines that the vehicle is running, the signal processing and calculating portion 11 broadly determines the cardiac status of the driver based on, for example, the intervals between R-wave peaks (the wave height of the R-wave) in the electrocardiogram waveform. On the other hand, when the vehicle state determining portion 5 determines that the vehicle is stopped, the signal processing and calculating portion 11 more strictly determines the cardiac status of the driver based on the entire electrocardiogram waveform including the R-wave peaks (the wave height of the R-wave) in the electrocardiogram waveform.

Here, the electrocardiogram waveform mainly includes a P-wave that reflects the electrical excitation of the atrium of the heart, Q-, R-, and S-waves (hereinafter referred to as the "QRS complex") that reflect the electrical excitation of the ventricles of the heart, and a T-wave that reflects the repolarization process of myocardial cells of the excited ventricles. The wave height (electrical potential) of the R-wave is the largest and is thus the strongest with respect to noise from myoelectric noise and the like. The T-wave has the next largest wave height and the P-wave has the smallest wave height.

The reason the signal processing and calculating portion 11 broadly determines the cardiac status of the driver based on the intervals between R-wave peaks while the vehicle is running is because the R-wave peaks are the portions with the largest wave heights in the electrocardiogram waveform and are thus the strongest with respect to noise from myoelectric noise and the like. Also, the reason the signal processing and calculating portion 11 more strictly determines the cardiac status of the driver based on the entire electrocardiogram waveform including the R-wave peaks when the vehicle is stopped is because when the vehicle is stopped, the driver tends to be at ease so there is less noise from myoelectric noise and the like. Therefore a determination can be made based on the overall electrocardiogram waveform including the T-wave and P-wave which have smaller wave heights than the R-wave.

The template storing portion 12 stores a template having a reference electrocardiogram waveform in a storage device such as RAM (Random Access Memory) or a HDD (Hard Disk Drive), not shown. The reference electrocardiogram waveform may be a standard electrocardiogram waveform that was stored in advance or an electrocardiogram waveform that was first obtained from the driver. Initially only one template is prepared, but a plurality of templates may also be prepared to correspond to different drivers.

Here, the term "reference electrocardiogram waveform" refers to an electrocardiogram waveform that represents the template to which it belongs, and is a waveform indicated by either the measured values of, for example, the wave heights of the P-, Q-, R-, and S-waves, or the average value of those measured values, with a portion that include the P-, Q-, R-, S-, and T-waves as a single unit. In addition to the reference electrocardiogram waveform, each template also contains information such as the maximum value, minimum value, and standard deviation of each wave height. Also, each template also contains information such as the wave widths, PQ interval, QT interval, RR interval (RRI (R-R interval)), average height (average signal strength), and heart rate, which are secondarily calculated from the measured values. Further, each template may also use a differential waveform of the electrocardiogram waveform as the reference electrocardiogram waveform.

The electrocardiogram waveform obtaining portion 10 captures a range of the R-wave peak ±300 milliseconds, for example, from the electrocardiogram waveform that was obtained from the cardiac sensor 1 and amplified by the cardiac amplifier 3, and outputs that range to an electrocardiogram waveform comparing portion 13 as a single unit.

The electrocardiogram waveform comparing portion 13 compares the electrocardiogram waveform received from the electrocardiogram waveform obtaining portion 10 with the reference electrocardiogram waveform of the one template stored in the template storing portion 12 and determines whether they are similar. The electrocardiogram waveform comparing portion 13 calculates a correlation coefficient between the received electrocardiogram waveform and the reference electrocardiogram waveform of the one template, for example, and determines that they are similar if the correlation coefficient is equal to or greater than a predetermined value (such as 0.75). Also, information such as the wave height and the like of the P-, Q-, R-, S-, and T-waves may also be used in the comparison of the electrocardiogram waveforms. Further, when there are a plurality of templates (reference electrocardiogram waveforms) that are determined to be similar, the reference electrocardiogram waveform of the template with the highest correlation coefficient is selected as the reference electrocardiogram waveform determined to be similar to the received electrocardiogram waveform.

The template updating portion 14 updates the average values and standard deviations and the like of the wave heights and wave widths, PQ interval, QT interval, and RRI and the like of each of the P-, Q-, R-, S-, and T-waves of the reference electrocardiogram waveform that was determined to be similar by the electrocardiogram waveform comparing portion 13, based on the electrocardiogram waveform received from the electrocardiogram waveform obtaining portion 10.

In addition, the updating takes into account the number of electrocardiogram waveforms included in the average value and the like of the reference electrocardiogram waveform. For example, when the reference electrocardiogram waveform is formed with the average value of 19 preceding electrocardiogram waveforms, the received electrocardiogram waveform has a degree of incidence of $\frac{1}{20}$ (i.e., 5%). Alternatively, updating may be done without relying on the number of electrocardiogram waveforms included in the average value and the like, with a degree of incidence of the pre-stored reference electrocardiogram waveform being 80% and the degree of incidence of the received electrocardiogram waveform being 20%.

Also, if the electrocardiogram waveform comparing portion 13 determines that the electrocardiogram waveform received from the electrocardiogram waveform obtaining portion 10 does not resemble the reference electrocardiogram waveforms of any of the templates, the template updating portion 14 creates a new template and uses the electrocardiogram waveform received from the electrocardiogram waveform obtaining portion 10 as the reference electrocardiogram waveform of that template. Furthermore, when there is no template stored in the template storing portion 12, such as when the power is turned on, the template updating portion 14 may create a new template and use the first received electrocardiogram waveform as the reference electrocardiogram waveform. Also, even if a new template is created, the template updating portion 14 does not have to use the electrocardiogram waveform received from the electrocardiogram waveform obtaining portion 10 as the reference electrocardiogram waveform of that template, but may instead create a reference electrocardiogram waveform from the received electrocardiogram waveform and a predetermined electrocardiogram waveform that was stored in advance.

In this way, the heart rhythm monitoring device 100 uses an electrocardiogram waveform that is similar to a reference electrocardiogram waveform of a pre-existing template to update the pre-existing template, which prevents countless templates having similar reference electrocardiogram waveforms from being created.

The update counting portion 15 counts, for each template, the number of electrocardiogram waveforms that the template updating portion 14 uses to update the reference electrocardiogram waveform of each template.

When an electrocardiogram waveform which has been affected by noise from myoelectric noise and the like has become a reference electrocardiogram waveform of a template created in the absence of a similar template, the template erasing portion 16 erases that template based on a predetermined condition.

For example, the template erasing portion 16 references the time that has elapsed after the template selected to be erased was updated last. When that elapsed time exceeds a predetermined period of time (such as 20 seconds), the template erasing portion 16 erases the template selected to be erased. Alternatively, the template erasing portion 16 obtains the number of electrocardiogram waveforms used to update the template selected to be erased from the update counting portion 15 and erases that template selected to be erased if the number of electrocardiogram waveforms used in the update in a predetermined period of time has not reached a predetermined number (such as 10).

In this way, the heart rhythm monitoring device 100 detects templates created from electrocardiogram waveforms that had been affected by noise and erases them, thereby preventing an electrocardiogram waveform that was affected from noise as being erroneously determined as an erratic heart rhythm.

When an electrocardiogram waveform that was determined by the electrocardiogram waveform comparing portion 13 as not resembling one template is used to update another template, the template merging portion 17 merges the other template that originally should belong to the one template with the one template.

In this case, the comparison by the electrocardiogram waveform comparing portion 13 may be too precise. For example, if an electrocardiogram waveform that likely belongs to one template under normal environmental conditions (i.e., noise conditions) is obtained under environmental conditions where noise tends to be produced, another template may end up being updated for a portion of the electrocardiogram waveform as a template that does not resemble the one template.

In this case, the control apparatus 9 determines using information from the vehicle state determining portion 5 and the like that the current environmental conditions include a large amount of noise so the template merging portion 17 merges one template with the other template. At this time, the control apparatus 9 may also set the threshold value of a correlation function used by the electrocardiogram waveform comparing portion 13 lower than normal (such as 0.7 when the normal threshold value is 0.75) in order to make an analogical determination between the electrocardiogram waveform received from the electrocardiogram waveform obtaining portion 10 and the reference electrocardiogram waveform.

The merging by the template merging portion 17 is performed by merging the average value and standard deviation and the like of the wave heights, wave widths, PQ interval, QT interval, and RRI etc., of each of the P-, Q-, R-, S-, and T-waves of the reference electrocardiogram waveform of one template with the average value and standard deviation and the like of the wave heights, wave widths, PQ interval, QT interval, and RRI etc. of each of the P-, Q-, R-, S-, and T-waves of the reference electrocardiogram waveform of another template. Furthermore, the number of electrocardiogram waveforms that form each of the templates is taken into account when merging is performed. For example, when the number of electrocardiogram waveforms that form one template is 20 and the number of electrocardiogram waveforms that form the other template is 80, the reference electrocardiogram waveform created by merging is 20% affected by the reference electrocardiogram waveform of the one template and 80% affected by the reference electrocardiogram waveform of the other template.

The template merging portion 17 merges the other template with the one template if the correlation coefficient between the reference electrocardiogram waveform of the one template and the reference electrocardiogram waveform of the other template is equal to or greater than a predetermined value (such as 0.7). Incidentally, the threshold value of the correlation coefficient used here may be set to a smaller value than the threshold value used by the electrocardiogram waveform comparing portion 13 in order to make an analogical determination between the electrocardiogram waveform received from the electrocardiogram waveform obtaining portion 10 and the reference electrocardiogram waveform.

Alternatively, the template merging portion 17 may also determine whether to merge the templates based on the average height of the reference electrocardiogram waveform. Here the term "average height" refers to the average value of the height (the difference in the potential with respect to the reference potential) of one unit of an electrocardiogram waveform, which includes the P-, Q-, R-, S-, and T-waves. Incidentally, negative potentials that are lower than the reference potential may be treated as negative values and the absolute values of those values may be added.

The template merging portion 17 may also use a determining expression such as abs(H1−H2)/(H1+H2)<0.1, for example, from the average height H1 of the reference electrocardiogram waveform of the one template and the average height H2 of the reference electrocardiogram waveform of the other template. If the determining expression is satisfied, the template merging portion 17 may merge the two templates. In this expression, abs(H1−H2) is the absolute value of the difference in average heights.

In this way, even when an electrocardiogram waveform that should originally belong to one template is determined to belong to another template, the heart rhythm monitoring device 100 can reduce the amount of information stored in the template storing portion 12 as well as the number of templates to be compared by the electrocardiogram waveform comparing portion 13 by merging these two templates after the fact.

Next, a method according to which the heart rhythm monitoring device 100 determines whether a driver has an erratic heart rhythm will be described.

FIG. 2 is a flowchart illustrating a routine for determining whether a driver has an erratic heart rhythm while the vehicle is running, and FIG. 3 is a flowchart illustrating a routine for determining whether the driver has an erratic heart rhythm while the vehicle is stopped.

First, the routine for determining whether the driver has an arrhythmia while the vehicle is running will be described. The heart rhythm monitoring device 100 initially determines whether the vehicle is running using the vehicle state determining portion 5.

First, the control apparatus 9 obtains an electrocardiogram waveform that was obtained by the electrocardiogram waveform obtaining portion 10 and amplified by the cardiac amplifier 3 (step S1). Then the signal processing and calculating portion 11 detects only the R-wave peaks from the electrocardiogram waveform obtained by the electrocardiogram waveform obtaining portion 10 (step S2). The signal processing and calculating portion 11 continuously detects the R-wave peaks for a predetermined period of time and calculates a heart rate per minute. Also, the signal processing and calculating portion 11 monitors the fluctuation in the heart rate from the RRI, analyzes the frequency of this fluctuation in heart rate, and calculates a low frequency component (LF) and a high frequency component (HF). This signal processing and calculating portion 11 then determines whether the heart rhythm is erratic based on the calculated heart rate and the LF/HF ratio (step S3).

If any one of three conditions, i.e., i) the heart rate rises 25% or more than the average heart rate of the preceding five minutes, ii) the heart rate is equal to or greater than 100 beats per minute or equal to or less than 40 beats per minute, or iii) the LF/HF ratio rises 50% or more compared with the LF/HF ratio of the preceding 30 to 40 minutes, is satisfied (i.e., YES in step S3), the signal processing and calculating portion 11 determines that there may be an arrhythmia, in which case the control apparatus 9 displays a warning on the display device 8 and operates the vehicle stopping assist portion 7 (step S4) to stop the vehicle.

If none of the foregoing conditions are satisfied (i.e., NO in step S3), the signal processing and calculating portion 11 continuously monitors the R-wave without the control apparatus 9 operating the vehicle stopping assist portion 7.

Next, the routine for determining whether the driver has an arrhythmia while the vehicle is stopped will be described. When the vehicle stopping assist portion 7 stops the vehicle as described above, the control apparatus 9 obtains the electrocardiogram waveform that has been obtained by the electrocardiogram waveform obtaining portion 10 via the cardiac sensor 1 and amplified by the cardiac amplifier 3, while simultaneously obtaining a pulse waveform that was obtained by the pulse wave sensor 2 and amplified by the pulse wave amplifier 4 (step S11).

Next, the signal processing and calculating portion 11 detects the ST level from the electrocardiogram waveform obtained by the electrocardiogram waveform obtaining portion 10 and estimates the blood pressure from the pulse wave waveform (step S12). Then the signal processing and calculating portion 11 determines whether the condition is pathological based on the detected ST level or the estimated blood pressure (step S13).

If the level of the ST segment is a reference potential of +0.2 mV or greater or −0.2 mV or less, or the blood pressure rises 25% or more or falls 25% or more (i.e., YES in step S13), then the signal processing and calculating portion 11 determines that cardiaccondition is serious and automatically notifies a pre-registered contact such as family, the individual's physician, HelpNet or the like, or sounds the horn and flashes the lights to alert others that there is an emergency (step S14).

If one of the foregoing conditions is not satisfied (i.e., No in step S13), the signal processing and calculating portion 11 continues to measure the ST segment and blood pressure without notifying anyone via the communication device 6. Incidentally, it is also possible to have the signal processing and calculating portion 11 not allow the vehicle to take off from a standstill again until a predetermined period of time (such as 10 minutes) has passed after the vehicle has been stopped with the assistance of the vehicle stopping assist portion 7.

Next, a method according to which the heart rhythm monitoring device 100 determines whether the heart rhythm is erratic using an electrocardiogram waveform template will be described. The determination according to this template may be based on the QRS complex in the electrocardiogram waveform obtained while the vehicle is running, or may be based on the entire electrocardiogram waveform obtained while the vehicle is stopped.

FIG. 4 is a flowchart illustrating a routine according to which the heart rhythm monitoring device 100 updates a template of an electrocardiogram waveform.

First, the electrocardiogram waveform obtaining portion 10 obtains an electrocardiogram waveform that was obtained by the cardiac sensor 1 and amplified by the cardiac amplifier 3 (step S21), and then captures a range of the R-wave peak ±300 milliseconds from the electrocardiogram waveform. This range includes the QRS group in the electrocardiogram waveform and thus includes a waveform component that is strong with respect to noise from myoelectric noise and the like.

Next, the control apparatus 9 references the template storing portion 12 and determines whether or not there is a pre-existing template (step S23). If the control apparatus 9 finds that there is no pre-existing template (i.e., NO in step S23), then the template updating portion 14 creates a new template and the electrocardiogram waveform captured by the electrocardiogram waveform obtaining portion 10 is used as the reference electrocardiogram waveform of the newly created template (step S28). If, on the other hand, the control apparatus 9 finds that there is a pre-existing template (i.e., YES in step S23), the electrocardiogram waveform comparing portion 13 calculates the degree of similarity between the electrocardiogram waveform that was captured by the electrocardiogram waveform obtaining portion 10 and the reference electrocardiogram waveform of the pre-existing template (step S24). The degree of similarity is a correlation coefficient between the electrocardiogram waveform captured by the electrocardiogram waveform obtaining portion 10 and the reference electrocardiogram waveform of the pre-existing template.

Next, the control apparatus 9 references the template storing portion 12 and determines whether there is another pre-existing template (step S25). If the control apparatus 9 finds that there is another pre-existing template (i.e., YES in step S25), then the degree of similarity calculation in step S24 is repeated. If, on the other hand, the control apparatus 9 finds that there is no other pre-existing template, the electrocardiogram waveform comparing portion 13 determines whether the calculated degree of similarity is equal to or greater than a predetermined value (such as a correlation coefficient of 0.75) (step S26).

If the electrocardiogram waveform comparing portion 13 determines that the calculated degree(s) of similarity is less than the predetermined value (i.e., NO in step S26), the template updating portion 14 creates a new template and uses the electrocardiogram waveform captured by the electrocardiogram waveform obtaining portion 10 as the reference electrocardiogram waveform of the newly created template (step S28). If, on the other hand, the degree of similarity of the one template is equal to or greater than the predetermined value (i.e., YES in step S26), the template updating portion 14 updates the one template based on the electrocardiogram waveform captured by the electrocardiogram waveform obtaining portion 10 (step S27). If there are a plurality of templates in which the degree of similarity is equal to or greater than the predetermined value, the template updating portion 14 updates the template having the highest degree of similarity based on the electrocardiogram waveform captured by the electrocardiogram waveform obtaining portion 10 (step S27).

The heart rhythm monitoring device 100 then determines whether the heart rhythm is erratic based on the template updated by the method described above and various characteristics of cardiac disorder (heart disease) described below.

Normally, the electrocardiogram waveform of a healthy individual or an individual with symptoms of atrial fibrillation (related to the P-wave), sinus arrhythmia or atrial premature contraction (hereinafter simply referred to as "atrial fibrillation or the like") does not affect the electrocardiogram waveform of the QRS complex so only one template is created. However, the RRI of individuals with symptoms of atrial fibrillation or the like is often times not constant. Therefore, information related to the RRI of the template can be used to distinguish those individuals with symptoms of atrial fibrillation or the like from healthy individuals.

Also, in the electrocardiogram waveform of individuals with symptoms of premature ventricular contraction or bundle branch block (hereinafter referred to as "premature ventricular contraction"), the form of the QRS complex produced by premature ventricular contraction or the like greatly changes. Therefore, two or more templates are created, i.e., a template from a normal QRS complex in which there is no premature ventricular contraction or the like and a template from a QRS complex when premature ventricular contraction or the like has occurred. Furthermore, in the electrocardiogram waveform of an individual with symptoms of premature ventricular contraction or the like, the average wave height and the average RRI and the like differ greatly when premature ventricular contraction or the like occurs as opposed to when premature ventricular contraction or the like does not occur.

Here, the term atrial fibrillation refers to an arrhythmia in which the atrium is irregularly excited at a frequency of 450 to 600 times per minute, and that excitation wave is randomly transmitted to atrioventricular node, thus making the ventricular excitation irregular. The term extrasystolic beat refers to an arrhythmia in which an extra beat is generated before the normal beat due to the myocardium becoming activated by electrical stimuli from an abnormal portion. When it originates in the atrium it is referred to as atrial premature contraction and when it originates in the ventricle it is referred to as premature ventricular contraction. Also, sinus arrhythmia refers to a case in which the fluctuation range of RRI (i.e., the difference between the longest and shortest RRI) is 20% or more. Bundle branch block refers to a conduction disturbance in which electrical stimuli that passes through a bundle branch that transmits electrical stimuli to the ventricles is partially or completely interrupted.

FIG. 5 is a flowchart illustrating a routine according to which the heart rhythm monitoring device 100 determines whether a driver has an erratic heart rhythm based on the information in the template.

First, the signal processing and calculating portion 11 references the template storing portion 12 and obtains the number of pre-existing templates (step S31). If the signal processing and calculating portion 11 finds two or more pre-existing templates (i.e., NO in step S31), it determines that there is a possibility of premature ventricular contraction or a bundle branch block (step S35). If, on the other hand, the signal processing and calculating portion 11 finds that there is only one pre-existing template (i.e., YES in step S31), it then references information relating to the RRI of the template and determines whether the heart rhythm is erratic based on a predetermined calculation value (such as a value obtained as the quotient of the standard deviation of RRI divided by the average value of RRI) (step S32).

If the signal processing and calculating portion 11 determines that the quotient of the standard deviation of RRI divided by the average value of RRI is less than 0.2, for example, (i.e., YES in step S32), then the signal processing and calculating portion 11 determines that the heart rhythm is not erratic (step S33). If, on the other hand, the signal processing and calculating portion 11 determines that the quotient of the standard deviation of RRI divided by the average value of RRI is equal to or greater than 0.2 (i.e., NO in step S32), then the signal processing and calculating portion 11 determines that there is a possibility of atrial fibrillation, sinus arrhythmia, or atrial premature contraction (step S34). This calculation value is not limited to being obtained using information related to the RRI of the average value, standard deviation, or coefficient of variation (CV) of the RRI, for example, as long as it can distinguish between the various symptoms of cardiac disorder described above using, for example, information relating to the average height.

In this way, the heart rhythm monitoring device 100 monitors the heart rhythm of a driver and determines whether the heart rhythm is erratic without the driver even being aware that his or her electrocardiogram waveform is being monitored, by providing electrodes of the cardiac sensor 1 on the surface of the steering wheel.

Also, the heart rhythm monitoring device 100 roughly determines whether the heart rhythm has become erratic by monitoring the R-wave peaks while the vehicle is running. If according to this rough determination indicates that the heart rhythm is erratic, the heart rhythm monitoring device 100 first prompts the vehicle to stop and then measures the electrocardiogram waveform in detail while the driver is at ease, and thus can accurately determine whether the heart rhythm is erratic. As a result, it is possible to prevent more accidents from occurring due to a driver suddenly going into cardiac arrest or the like while driving a vehicle.

Also, the heart rhythm monitoring device 100 is able to detect a more detailed state of an erratic heart rhythm by using the template, and thus can transmit more useful information to the physician or the like via the communication device 6.

While the invention has been described with reference to example embodiments thereof, it is to be understood that the invention is not limited to the described embodiments or constructions. To the contrary, the invention is intended to cover various modifications and equivalent arrangements. In addition, while the various elements of the example embodiments are shown in various combinations and configurations, other combinations and configurations, including more, less or only a single element, are also within the spirit and scope of the invention.

For example, the portions 10 to 17 that form the control apparatus 9 may be a program stored in a medium that is readable by a computer, and the various portions stored in a HDD or the like and transferred into RAM or the like may be executed by the computer of the control apparatus 9.

What is claimed is:

1. A heart rhythm monitoring device for a vehicle, which determines whether a driver has an arrhythmia based on an electrocardiogram waveform having a waveform component that is strong with respect to noise and a waveform component that is not strong with respect to noise, comprising:
    a vehicle state determining portion that determines whether the vehicle is stopped;
    an electrode that is arranged on a steering wheel in a position where the driver grips the steering wheel;
    an electrocardiogram waveform obtaining portion that obtains a first electrocardiogram waveform from the electrode; and
    a signal processing and calculating portion that determines whether the heart rhythm of the driver is erratic based on the first electrocardiogram waveform,
    wherein when the vehicle state determining portion determines that the vehicle is not stopped, the signal processing and calculating portion determines whether the heart rhythm of the driver is erratic based on the waveform component that is strong with respect to noise in the first electrocardiogram waveform, and
    wherein when the vehicle state determining portion determines that the vehicle is stopped, a second electrocardiogram waveform is obtained and the signal processing and calculating portion determines whether the heart rhythm of the driver is erratic based on a waveform component other than the waveform component that is strong with respect to noise in the second electrocardiogram waveform.

2. The heart rhythm monitoring device according to claim 1, wherein the waveform component that is strong with respect to noise is an R-wave component of the first electrocardiogram waveform.

3. The heart rhythm monitoring device according to claim 1, further comprising:
a vehicle stopping assist portion that assists the driver in stopping the vehicle,
wherein the vehicle stopping assist portion assists the driver in stopping the vehicle when the vehicle state determining portion determines that the vehicle is not stopped and the signal processing and calculating portion determines that the heart rhythm of the driver is erratic.

4. The heart rhythm monitoring device according to claim 1, further comprising:
a pulse wave sensor that obtains a pulse wave waveform from the electrode,
wherein when the vehicle state determining portion determines that the vehicle is stopped, the determination of whether the heart rhythm of the driver is erratic is also based on the pulse wave waveform.

5. The heart rhythm monitoring device according to claim 1, further comprising:
a template storing portion that stores at least one template having a reference electrocardiogram waveform;
an electrocardiogram waveform comparing portion that determines whether the first electrocardiogram waveform resembles the reference electrocardiogram waveform of each of the at least one template stored in the template storing portion; and
a template updating portion,
wherein when the electrocardiogram waveform comparing portion determines that the first electrocardiogram waveform resembles the reference electrocardiogram waveform of a first template of the at least one template stored in the template storing portion, the template updating portion updates the reference electrocardiogram waveform of the first template based on the first electrocardiogram waveform, and when the electrocardiogram waveform comparing portion determines that the first electrocardiogram waveform does not resemble the reference electrocardiogram waveform of each of the at least one template stored in the template storing portion, the template updating portion creates another template and uses the first electrocardiogram waveform as the reference electrocardiogram waveform of the another template.

6. The heart rhythm monitoring device according to claim 5, wherein the electrocardiogram waveform comparing portion determines whether the first electrocardiogram waveform resembles the reference electrocardiogram waveform of the first template based on a correlation coefficient calculated between the reference electrocardiogram waveform of the first template and the first electrocardiogram waveform.

7. The heart rhythm monitoring device according to claim 5, wherein the electrocardiogram waveform comparing portion determines that the first electrocardiogram waveform resembles the reference electrocardiogram waveform of the first template when a predetermined relationship between an average height of the reference electrocardiogram waveform of the first template and the average height of the first electrocardiogram waveform is satisfied.

8. The heart rhythm monitoring device according to claim 5, wherein the signal processing and calculating portion determines whether there is atrial fibrillation based on information related to an R-wave interval when there is one template stored in the template storing portion.

9. The heart rhythm monitoring device according to claim 5, wherein when there are two or more templates stored in the template storing portion, the signal processing and calculating portion determines whether there is premature ventricular contraction based on the difference between two reference electrocardiogram waveforms from among the two or more templates.

10. The heart rhythm monitoring device according to claim 5, further comprising:
an update counting portion that totals the number of electrocardiogram waveforms used to update the reference electrocardiogram waveform of the first template; and
a template erasing portion that erases the first template stored by the template storing portion,
wherein the template erasing portion erases the first template i) when a predetermined period of time has passed after the reference electrocardiogram waveform of the first template was last updated, or ii) when the number of electrocardiogram waveforms totaled in the predetermined period of time by the update counting portion does not reach a predetermined number.

11. The heart rhythm monitoring device according to claim 5, further comprising:
a template merging portion that merges the first template and a second template of each of the at least one template stored in the template storing portion into a single template,
wherein the template merging portion merges the first template with the second template by updating the reference electrocardiogram waveform of the second template based on the reference electrocardiogram waveform of the first template when the template merging portion has determined that the reference electrocardiogram waveform of the first template resembles the reference electrocardiogram waveform of the second template.

12. The heart rhythm monitoring device according to claim 11, wherein the template merging portion merges the first template with the second template based on a ratio of the total number of electrocardiogram waveforms used to update the reference electrocardiogram waveform of the first template to the total number of electrocardiogram waveforms used to update the reference electrocardiogram waveform of the second template.

13. A method for monitoring heart rhythm in a vehicle, which determines whether a driver has an arrhythmia based on an electrocardiogram waveform having a waveform component that is strong with respect to noise and a waveform component that is not strong with respect to noise, comprising:
determining whether the vehicle is stopped;
obtaining an electrocardiogram waveform from an electrode that is arranged on a steering wheel in a position where the driver grips the steering wheel; and
determining whether the heart rhythm of the driver is erratic based on the obtained electrocardiogram waveform,
wherein when it is determined that the vehicle is not stopped, it is determined whether the heart rhythm of the driver is erratic based on the waveform component that is strong with respect to noise in the obtained electrocardiogram waveform, and
wherein when it is determined that the vehicle is stopped, it is determined whether the heart rhythm of the driver is erratic based on a waveform component other than the waveform component that is strong with respect to noise in the obtained electrocardiogram waveform.

* * * * *